United States Patent
Wolf (10) Patent No.: US 9,828,119 B2
(45) Date of Patent: Nov. 28, 2017

(54) METERING DEVICE FOR POWDER AND METHOD FOR METERING POWDER

(71) Applicant: Harro Höfliger Verpackungsmaschinen GmbH, Allmersbach im Tal (DE)

(72) Inventor: Achim Wolf, Allmersbach im Tal (DE)

(73) Assignee: HARRO HÖFLIGER VERPACKUNGSMASCHINEN GMBH, Allmersbach im Tal (DE)

(*) Notice: Subject to any disclaimer, the term of this patent is extended or adjusted under 35 U.S.C. 154(b) by 201 days.

(21) Appl. No.: 14/611,310

(22) Filed: Feb. 2, 2015

(65) Prior Publication Data
US 2015/0217879 A1    Aug. 6, 2015

(30) Foreign Application Priority Data
Feb. 1, 2014    (EP) .................................. 14000375

(51) Int. Cl.
*B65B 1/36* (2006.01)
*A61M 15/00* (2006.01)
(Continued)

(52) U.S. Cl.
CPC ........... *B65B 1/36* (2013.01); *A61M 15/0001* (2014.02); *B65B 1/363* (2013.01); *B65B 37/08* (2013.01);
(Continued)

(58) Field of Classification Search
CPC .......... B65B 1/36; B65B 37/08; B65B 37/20; B65B 1/363; B65B 1/20; G01F 11/10; A61M 15/0001; A61M 2209/045
(Continued)

(56) References Cited

U.S. PATENT DOCUMENTS 3,718,164 A    2/1973    Stewart
4,227,835 A *  10/1980   Nussbaum ............. B05B 7/144
                                                 222/636
(Continued)

FOREIGN PATENT DOCUMENTS

DE            10327070 A1 * 12/2003
DE      10 2010 000 682 A1    7/2011
(Continued)

OTHER PUBLICATIONS

European Search Report, Appl. No. 14000375.7, dated May 28, 2014, 4 pgs.

*Primary Examiner* — Jason K Niesz
*Assistant Examiner* — James Hakomaki
(74) *Attorney, Agent, or Firm* — Paul D. Strain, Esq.; Strain & Strain PLLC (57) ABSTRACT

A metering device for the volumetric metering of powder, including pharmaceutical powder, and the simultaneous metering and filling of target cavities with metered powder, as well as a metering system and an associated method are shown. One embodiment of the metering device includes a metering station with a powder storage container, a filling station, and a movable metering member. The metering member has a flat transfer surface that includes metering cavities, which correspond in number and geometry to target cavities arranged in the filling station, and also to metering openings in the metering station. The metering cavities each have an open end and a base, wherein an air-permeable filter element forms at least a part of the base of each. The metering member includes a central pressure channel connected to the metering cavities through the filter elements for applying a negative or positive pressure to the metering cavities.

20 Claims, 4 Drawing Sheets (51) Int. Cl.
*B65B 1/04* (2006.01)
*B65B 37/08* (2006.01)
*B65B 37/20* (2006.01)
*G01F 11/10* (2006.01)

(52) U.S. Cl.
CPC .............. *B65B 37/20* (2013.01); *G01F 11/10* (2013.01); *A61M 2209/045* (2013.01)

(58) Field of Classification Search
USPC ............................... 141/234, 129, 18, 81, 80
See application file for complete search history.

(56) References Cited

U.S. PATENT DOCUMENTS

| | | | | |
|---|---|---|---|---|
| 4,528,848 | A * | 7/1985 | Hafner | G01F 11/24 110/101 CC |
| 4,751,948 | A * | 6/1988 | Hertig | B65B 1/36 128/203.15 |
| 5,775,389 | A * | 7/1998 | Griffin | G01F 11/282 141/100 |
| 6,089,675 | A * | 7/2000 | Schlanger | B60B 27/023 280/279 |
| 6,257,804 | B1 * | 7/2001 | Gathmann | B05B 7/144 406/138 |
| 6,971,554 | B2 * | 12/2005 | Rochat | B24C 7/0092 141/248 |
| 7,866,352 | B2 * | 1/2011 | Kimura | B29C 31/066 141/11 |
| 2010/0212777 | A1 * | 8/2010 | Weigel | B65B 1/36 141/94 |
| 2011/0139812 | A1 * | 6/2011 | Dagsland | B65B 1/363 141/237 |
| 2011/0146839 | A1 * | 6/2011 | Ansaloni | A61J 3/074 141/129 |
| 2011/0204094 | A1 * | 8/2011 | Meckstroth | B65B 1/08 141/12 |
| 2012/0132314 | A1 * | 5/2012 | Weigel | B65B 1/36 141/2 |

FOREIGN PATENT DOCUMENTS

EP 0 022 541 A2 1/1981
WO WO 97/41031 A1 11/1997

\* cited by examiner

METERING DEVICE FOR POWDER AND METHOD FOR METERING POWDER

CROSS-REFERENCE TO RELATED PATENT APPLICATIONS

This application is based upon and claims the benefit of priority from prior European Patent Application No. EP 14 000 375.7, filed Feb. 1, 2014, the entire contents of which are incorporated herein by reference in their entirety.

BACKGROUND

The application relates to a metering device for the volumetric metering of a pharmaceutical powder and filling of a plurality of target cavities with the metered powder, to a metering system, and to a method for metering such a powder using the metering device mentioned and for simultaneously filling a plurality of target cavities arranged in a common plane.

For the correct use of, for example, pharmaceutical powder by the target person, precisely metered partial quantities have to be provided, for example, in capsules, blister packs or other target cavities. First of all, volumetric metering of the powder is common for this purpose. The metered partial quantities are then poured into the target cavities.

If the target cavities are arranged in a row, use is commonly made of what are referred to as roller metering apparatuses. In this case, metering openings are provided on the circumferential surface of a metering roller along a line parallel to the longitudinal axis of the roller, said metering openings being filled with powder. The volume of the metering openings defines individual partial quantities of the powder, as a result of which volumetric metering is undertaken. The linear row of metering openings corresponds to the linear row of target cavities. After the metering openings have been filled, the metering roller is rotated until all of the metering openings lie above the target cavities. The volumetrically metered powder is then transferred out of the metering openings into the target cavities.

The metering and filling become problematic in particular whenever a relatively large number of target cavities which are not arranged in a line, but rather in a common plane, are intended to be filled simultaneously. This case occurs, for example, with what are referred to as DPI discs (dry powder inhaler discs), in which a plurality of target cavities, in particular 10 to 61 target cavities, are formed in a circular manner in a flat carrier disc and are surrounded by a seal surface. All of the target cavities in such a plane are intended to be filled simultaneously and are subsequently closed by sealing a sealing foil onto the seal surface. In such or comparable cases, the filling with roller metering apparatuses fails since the metering openings can be arranged only on an axially parallel line of the circumferential surface of the rollers and not in a plane. It would therefore only be possible simultaneously to fill two diametrically opposite target cavities. For the complete filling of all the target cavities lying in a plane, a plurality of sequential filling operations would therefore be required when a roller metering apparatus is used, and this is uneconomical.

One practicable way is the filling with what are referred to as pipettes although a correspondingly high number of individual pipettes is required with a correspondingly high outlay on investment. The use of pipettes is technically problematic in cases in which the target cavities have a non-circular basic outline. In addition, a sufficiently deep powder bed has to be provided, as a consequence of which an undesirably large residual quantity of powder cannot be avoided. Alternatively, use can be made of what are referred to as diaphragm metering apparatuses, in which the target cavities are covered with an air-permeable diaphragm. A powder channel is guided through the diaphragm. By applying a negative pressure difference to the diaphragm, powder is sucked into the target cavity through the powder channel and retained at the diaphragm. Apparatus and method are restricted to bringing about a filling of the target cavity to the edge. The connection of diaphragm and powder channel is technically problematic, with the effective diaphragm surface also being reduced by the cross section of the powder channel guided therethrough. The cross section of the powder channel therefore has to be selected to be as small as possible, but this opposes a reliable throughflow of the powder. Problems can also occur here in the filling of target cavities which are non-circular in basic outline if, in narrow basic outline regions, a sufficiently large space does not remain for the diaphragm on the other side of the powder channel.

SUMMARY OF PREFERRED EMBODIMENTS

It is one object of the present application to provide a metering device for the volumetric metering of an in particular pharmaceutical powder, which metering device opens up improved possibilities for the simultaneous filling of a plurality of target cavities arranged in a common plane.

This object and other objects are achieved by the subject matter of the application, including its embodiments and their equivalents.

It is another object of the present application to provide a metering system comprising a number of target cavities arranged in a common plane and a metering device coordinated geometrically therewith, wherein the target cavities can be filled simultaneously using the metering system.

This object and other objects are achieved by the subject matter of the application, including its embodiments and their equivalents.

It is another object of the present application to provide a metering and filling method, through which, with increased accuracy and reliability at high cycle rates, individual quantities of powder can be metered and filled simultaneously into a plurality of target cavities arranged in a common plane.

This object and other objects are achieved by the subject matter of the application, including its embodiments and their equivalents.

According to an exemplary embodiment of the application, it is provided that the metering device comprises a metering station with a powder storage container, a filling station, and a movable metering member, wherein the metering member is cyclically movable from the metering station to the filling station and back again. The metering member has a flat transfer surface in which a plurality of metering cavities corresponding to the number and geometrical distribution of the target cavities are incorporated. The metering station has a flat contact surface which is provided for sealing contact of the metering member using the transfer surface thereof. Corresponding to the number and geometrical distribution of the metering cavities, metering openings into which powder channels emerging from the powder storage container lead are formed in the contact surface. In the plane of the transfer surface, the metering cavities each have an open side and each have a base which is opposite with respect thereto, wherein the base of the respective metering cavity is formed at least in sections by an air-permeable filter element. A central pressure channel which is connected in a pressure-transmitting manner to the metering cavities through the filter elements is formed in the metering member. The target cavities and the metering device which is geometrically coordinated therewith together form the metering system according to the application.

In an exemplary embodiment of the associated method according to the application, the following method steps are provided: first, the metering member is placed with the flat transfer surface thereof in a sealing manner against the flat contact surface of the metering station. Using the central pressure channel, a negative pressure difference is applied through the filter elements, the metering cavities and the powder channels to the powder in the powder storage container, as a consequence of which the metering cavities are simultaneously filled by the powder channels assigned thereto with the powder from the powder storage container, wherein the powder is retained at the filter elements. The metering member is subsequently moved from the metering station to the filling station with a negative pressure difference being maintained, wherein the metering cavities are brought into overlap with associated target cavities. The negative pressure difference is eliminated and the powder is brought out of the metering cavities into the respectively assigned target cavities. Finally, the metering member is moved back to the metering station.

In another exemplary embodiment, in a departure from diaphragm fillers according to the prior art, the filter elements and the powder channels are not located on the same side of the target cavity, but rather on opposite sides thereof. There is no mechanical connection and also no geometrical interaction between the filter elements and the powder channels, and therefore said filter elements and powder channels can be designed independently of one another. The powder can be extensively sucked up through the filter element, and therefore edge-full filing is possible even in the case of geometrically complex basic outlines of the metering cavities. At the same time, however, the metering cavity acts only as an intermediate volume, the size of which can differ from the volume of the target cavity. A partial filling of the target cavities is therefore readily possible. The flat configuration of transfer surface and contact surface permits a precisely fitting and tight mutual contact, and therefore the powder can be sucked up precisely and without spills using the associated powder channels. In addition, because of the flat configuration, there are no geometrical restrictions in the two-dimensional distribution of the metering cavities, and therefore the latter can be positioned corresponding in number and geometrical distribution to the flat arrangement of the target cavities. The common pressurization using the central pressure channel permits simultaneous metering with an at least approximately identical pressure difference at each metering cavity. The same also applies to the simultaneous transfer of the metered partial quantities of powder out of the metering cavities into the target cavities. The desired metering and filling quantity can easily be realized by volumetric adaptation of the metering cavities, for example by the design thereof as an exchangeable or formatting part without changes to the target cavities being required.

In another embodiment, the metering member is pivotable about an axis of rotation, wherein, in a 0° rotation position, the metering member lies with the flat transfer surface thereof facing upward below the metering station, and wherein, in a 180° rotation position, the metering member lies with the flat transfer surface thereof facing downward above the filling station. In particular, a plurality of metering members are arranged around the axis of rotation and, for a sequential approach of the metering station and the filling station, are combined to form a jointly rotatable unit. In clocked rotation steps, short cycle times can be achieved. In the corresponding arrangement of a plurality of metering members, various operations, such as metering, filling, inspecting, cleaning or the like, can be carried out simultaneously in individual cycle steps.

In yet another preferred embodiment, the metering member is movable linearly in the direction of a vertical axis toward the flat contact surface of the metering station and is raisable from said contact surface. In the associated operating method, the metering member is first of all moved linearly in the direction of the vertical axis toward the flat contact surface of the metering station, wherein the metering cavities are then filled with powder by charging with a negative pressure difference. The negative pressure difference not only leads to the metering cavities being filled with the powder, it also causes the metering member to be sucked towards the contact surface of the metering station. This firstly increases the sealing effect at the surfaces pressed against each other. Secondly, however, it is more difficult for the metering member to be raised from the contact surface of the metering station. In order to make the raising operation easier following the metering operation, the negative pressure difference is eliminated briefly. After the raising operation, the metering member is moved from the metering station to the filling station with a negative pressure difference being reapplied and maintained. The negative pressure difference prevents the powder from dropping out of the metering cavities during the moving or rotating operation.

In still another embodiment, depending on the properties of the powder used, a uniform negative pressure difference at the metering station may be sufficient for the metering operation. A pulse-like negative pressure difference is preferably applied at the metering station for filling the metering cavities with the powder. This briefly increases the flowability of the powder and therefore a precise filling of the metering cavities.

According to another embodiment, various possibilities are suitable for transferring the powder from the metering cavities into the target cavities at the location of the filling station. Suitable possibilities include a pressure surge with a positive pressure difference, an air pressure oscillating between a positive and a negative pressure difference, a mechanical pulse or a mechanical vibration which is applied to the powder located in the metering cavities. It may be expedient here, depending on requirements, for the metering member to lie at a small distance from the target cavities at the metering station. This assists, for example, a displacement of the air located in the target cavities by the entering powder. In particular, however, the metering member is pressed with the flat transfer surface thereof in a sealing manner against seal surfaces of the target cavities at the filling station. This ensures that the metered powder passes exclusively into the target cavity without partial quantities thereof inadvertently escaping or passing onto the seal surfaces. The metering accuracy is increased while, in addition, a subsequent tight sealing of the target cavities with a sealing foil is reliably possible.

In another preferred embodiment, the flat transfer surface of the metering member is formed at least in sections by an elastically flexible sealing material running around the metering cavities in a closed manner. The sealing material can be airtight and powder tight or porous in an air-permeable manner, but tight against the passage of powder.

In addition, a combination of the two properties is possible, for example, by a configuration in the form of foam, wherein airtightness and powder tightness or else air permeability with simultaneous powder tightness are obtained depending on the state of compression. The metering cavities here preferably have an inflexible encircling edge, wherein the edge is provided for direct contact against the contact surface of the metering station, and wherein the sealing material runs around the edge. The elastic sealing material, in particular under the action of a mechanical contact pressure force, optionally assisted by suction force as a consequence of the applied negative pressure difference, ensures that spurious air is not sucked up in the region of the encircling edges, and instead powder is exclusively sucked up using the respective powder channel. At the same time, an escape of powder is avoided. The inflexible edge which is rigid in comparison brings about a precise three-dimensional limitation of the metering cavity with a just as precisely determined volume, which increases the volumetric metering accuracy. In the case of the air permeability with simultaneous powder tightness, it can in particular be achieved at the filling station that the air displaced out of the target cavities by the powder filled therein can escape while, at the same time, an escape of powder from the target cavities or an undesirable action upon the seal surfaces with powder is prevented.

Still yet another embodiment includes a metering device for the volumetric metering of a pharmaceutical powder and filling of a plurality of target cavities with the metered powder, wherein the plurality of target cavities are arranged in a common plane. Such device includes a metering station, wherein the metering station comprises a powder storage container, and also a filling station, wherein the filling station comprises the plurality of target cavities. The device also contains a movable metering member, wherein the metering member is cyclically movable from the metering station to the filling station and back again, wherein the metering member comprises a flat transfer surface, wherein a plurality of metering cavities are arranged in the flat transfer surface, wherein the number and geometric distribution of the metering cavities corresponds to the number and the geometric distribution of the target cavities. Additionally, the metering station according to the embodiment further comprises a flat contact surface that provides a sealing contact of the metering member through engagement with the flat transfer surface, wherein metering openings are formed in the contact surface, wherein the number and geometric distribution of the metering openings corresponds to the number and geometric distribution of the metering cavities, wherein powder channels connect the powder storage container and the metering openings. Furthermore, in the plane of the transfer surface, the metering cavities each have an open side and a base opposite from the open side, wherein the base of the respective metering cavity is formed at least in sections by an air-permeable filter element, wherein a central pressure channel is formed in the metering member and is connected in a pressure-transmitting manner to the metering cavities through the filter elements.

In a variation of the above embodiment, the metering member is pivotable about an axis of rotation, wherein, in a 0° rotational position, the metering member lies with the flat transfer surface facing upward below the metering station, and wherein, in a 180° rotational position, the metering member lies with the flat transfer surface facing downward above the metering station.

In another aspect of the above embodiment, a plurality of metering members are arranged around the axis of rotation and together form a jointly rotatable unit that allows for a sequential approach of the metering station and the filling station.

In still another aspect, the metering member is displaceable in the direction of a vertical axis such that the metering member may move toward the flat contact surface of the metering station and away from the flat contact surface.

According to another potential arrangement, the flat transfer surface of the metering member is formed at least in part by an elastically flexible sealing material encircling the metering cavities in a closed manner.

In another construction of the embodiment, the sealing material is airtight. Optionally, the sealing material is porous in an air-permeable manner.

Pursuant to another arrangement, the metering cavities comprise an inflexible, encircling edge, wherein the edge is provided for direct contact against the contact surface of the metering station, and wherein the sealing material encircles the edge.

Another embodiment includes a metering system comprising any of the embodiments of the metering device described previously and an associated member of target cavities arranged in a common plane.

Still yet a further embodiment includes a method for metering a pharmaceutical powder and for filling a plurality of target cavities arranged in a common plane using any of the embodiments of the metering device described previously, said method including placing the metering member with the flat transfer surface a in sealing manner onto the flat contact surface of the metering station. The method also includes applying a negative pressure difference to the powder in the powder storage container through the filter elements, the metering cavities, and the powder channels by using the central pressure channel, wherein the metering cavities are simultaneously filled with the powder from the powder storage container through the powder channels, wherein the powder is retained at the filter elements. Furthermore, the method includes moving the metering member from the metering station to the filling station while maintain a negative pressure difference, and bringing the metering cavities t into overlap with associated target cavities. In addition to the above, the method provides for eliminating the negative pressure difference such that the powder is brought from the metering cavities into the respectively assigned target cavities, and moving the metering member back to the metering station.

In another aspect of the above embodiment of the method, the method also includes moving the metering member linearly in the direction of the vertical axis toward the flat contact surface of the metering station, filling the metering cavities with the powder by charging with the negative pressure difference, removing the metering member linearly in the direction of the vertical axis from the flat contact surface of the metering station, wherein the negative pressure difference is eliminated, and, moving the metering member from the metering station to the filling station with a negative pressure difference being reapplied and maintained.

In still another embodiment of the method, a pulse-like negative pressure difference is applied at the metering station for filling the metering cavities with the powder. The method may also include a pressure surge with a positive pressure difference, an air pressure oscillating between a positive and a negative pressure difference, a mechanical pulse or a mechanical vibration is applied to the powder located in the metering cavities at the filling station for transferring the powder from the metering cavities into the target cavities. Such method may optionally provide that the metering member is pressed with the flat transfer surface thereof in a sealing manner against seal surfaces of the target cavities at the filling station.

Further objects, features, and advantages of the present application will become apparent from the detailed description of preferred embodiments which is set forth below, when considered together with the figures of drawing.

BRIEF DESCRIPTION OF THE DRAWINGS

Exemplary embodiments of the application are described in more detail below with reference to the drawing, in which.

DETAILED DESCRIPTION OF PREFERRED EMBODIMENTS

Figure 1:
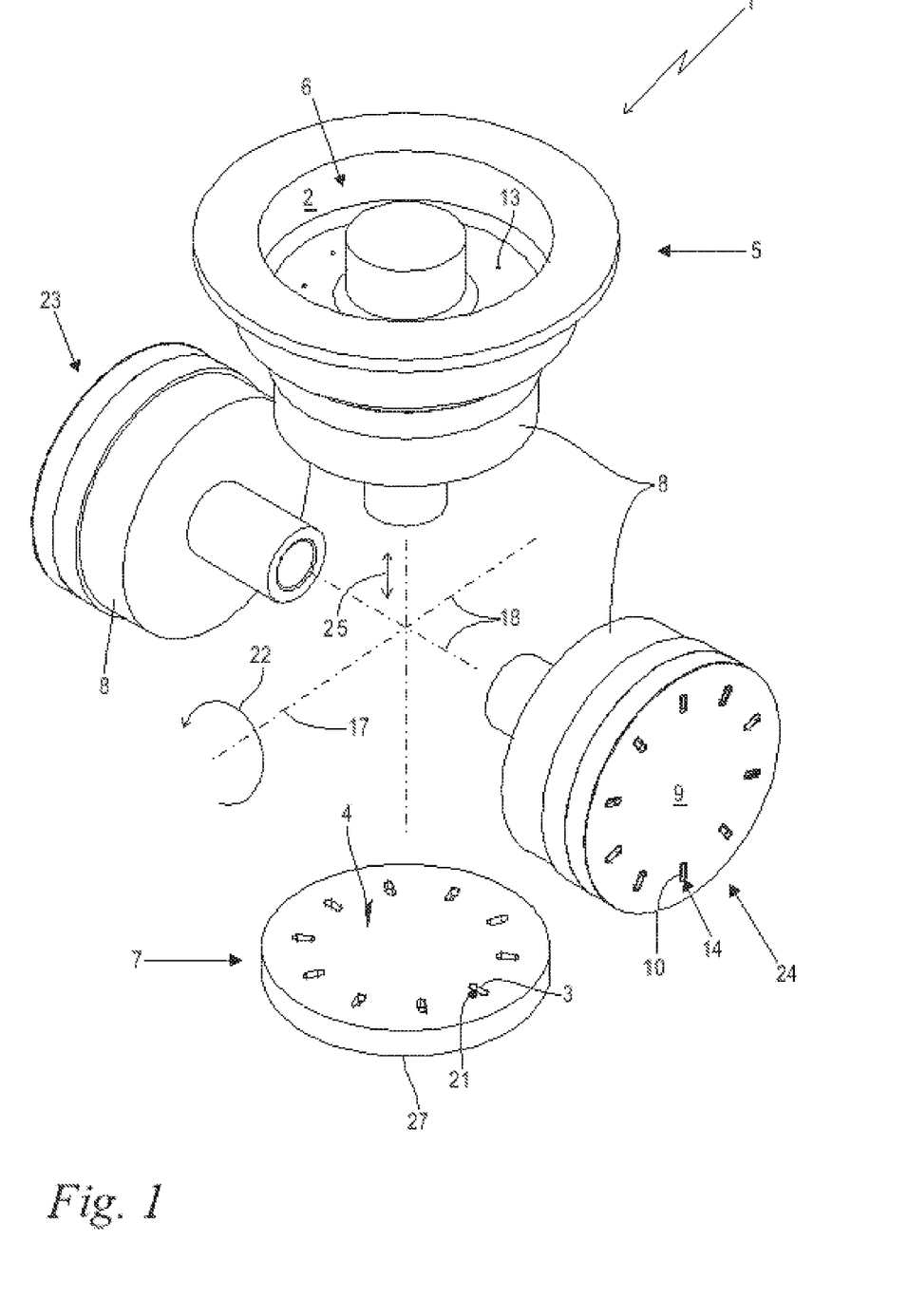
FIG. 1 shows, in a schematic overall view, an exemplary embodiment of a metering system according to the application with a metering station, with a filling station, in which a number of target cavities arranged in a common plane are held, and with at least one metering member, here four metering members, which are cyclically movable from the metering station to the filling station and back again.

FIG. 1 shows, in a schematic overall illustration, a first exemplary embodiment of a metering system according to the application which includes a metering device 1 and an associated number of target cavities 3 arranged in a common plane 4. The plurality of target cavities 3 accordingly do not lie on a common line, but rather span the plane 4 in two different horizontal directions in space such that the plane is therefore oriented horizontally or transversely with respect to the weight direction. Furthermore, a seal surface runs around the target cavities 3, which are initially open on one side. After the filling with a powder 2, a cover foil (not illustrated) is sealed onto the seal surface 21, as a result of which the filled target cavities 3 are tightly closed.

The ten target cavities 3 in this embodiment are formed here by way of example in an annular manner in a flat DPI disc 27 (dry powder inhaler disc). Such a DPI disc 27 is used in inhalers for pulmonary administration of pharmaceutical powder 2. DPI discs typically have ten to sixty one target cavities 3. Instead of the shown annular arrangement of the target cavities 3, any other geometrical arrangement, for example in rectangular, polygonal or matrix form, is also conceivable as long as the target cavities 3 lie in a common plane 4. In addition, it is not absolutely imperative that the target cavities 3 are formed in a common component, here in the DPI disc 27. Target cavities 3 as separate containers or groups thereof combined into components are also conceivable. Within the scope of the application, any other number of target cavities 3 can also be filled simultaneously in a metered manner. The target cavities 3 here have an elongate, oval basic outline by way of example. Any other basic outline of the target cavity 3 is also usable within the scope of the application. In addition, the application is not restricted to the metering of pharmaceutical powder for pulmonary administration. The application is also usable for metering other pharmaceutical powders or powdered food supplements, wherein the use of the term powder 2 can also include granules or the like.

The metering device 1 comprises a metering station 5 with a powder storage container 6 in which a stock of powder is kept ready. Furthermore, the metering device 1 also comprises a filling station 7 and at least one movable metering member 8. In the exemplary embodiment shown, a total of four metering members 8 are provided, according to the illustration in FIG. 2, of which the lower metering member 8 is not shown in FIG. 1 so as to better illustrate the DPI disc 27. The filling station 7 is arranged below the metering station 5 with respect to the weight direction. One or more intermediate stations 23, 24, the function of which is described in more detail further below, can optionally also be provided. The at least one metering member 8 is cyclically movable from the metering station 5 to the filling station 7 and back again, which can be realized by a linear stroke or the like. In the preferred exemplary embodiment shown, the metering member 8 is pivotable about an axis of rotation 17, wherein, in an upper 0° rotation position, the metering member 8 lies below the metering station 5, and wherein, in a lower 180° rotation position, the metering member 8 lies above the filling station 7. Further intermediate stations 23, 24 can be optionally be approached in corresponding intermediate angular steps. In the exemplary embodiment shown, a plurality of metering members 8, here, by way of example, four metering members 8, are arranged about the axis of rotation 17 and, for a sequential approach of the metering station 5, the filling station 7 and the optional intermediate stations 23, 24, are combined to form a unit which is jointly rotatable about the axis of rotation 17. In addition, each metering member 8 is linearly movable in the direction of a vertical axis 18 corresponding to a double arrow 25, wherein each vertical axis 18 of each metering member 8 lies radially with respect to the axis of rotation 17.

It can also be gathered from the illustration according to FIG. 1 that the metering members 8 each have a flat transfer surface 9 in which a plurality of metering cavities 10 corresponding to the number and to the geometrical distribution of the target cavities 3 are incorporated. In the plane of the transfer surface 9, the metering cavities 10 each have an open side 14 facing away from the basic body of the metering member 8. Preferably, but not imperatively, the metering cavities 10 have the same basic outline in the region of the open side 14 thereof as the target cavities 3. "Corresponding to the number and to the geometrical distribution or arrangement" in this embodiment means that each one of the metering cavities 10 can be brought into overlap with a respective target cavity 3 at the filling station 7. For this purpose, the metering cavities 10, like the target cavities 3, are formed in an annular manner at the same angular spacing and with the same radius in the transfer surface 9. The same applies to a differing distribution of the target cavities 3 on the plane 4. However, the above does not mean that the same number of metering cavities 10 and target cavities 3 necessarily have to be present. It may also be expedient that, on the basis of the number of target cavities 3, an n-times divisor (½, ⅓ or the like) is provided as the number of metering cavities 10. In this case, in a first cycle, a first portion of the target cavities 3 can be filled and the remaining target cavities 3 can be filled in one or more subsequent cycles.

It can furthermore also be gathered from the illustration of FIG. 1 that a number of powder channels 13 (not shown in FIG. 1) the function of which is explained in more detail further below, are formed in the base of the powder storage container 6. Each metering cavity 10 is assigned at least one powder channel, in this embodiment precisely one powder channel 13. However, it may also be expedient for each metering cavity 10 to be assigned two or more powder channels 13.

Figure 2:
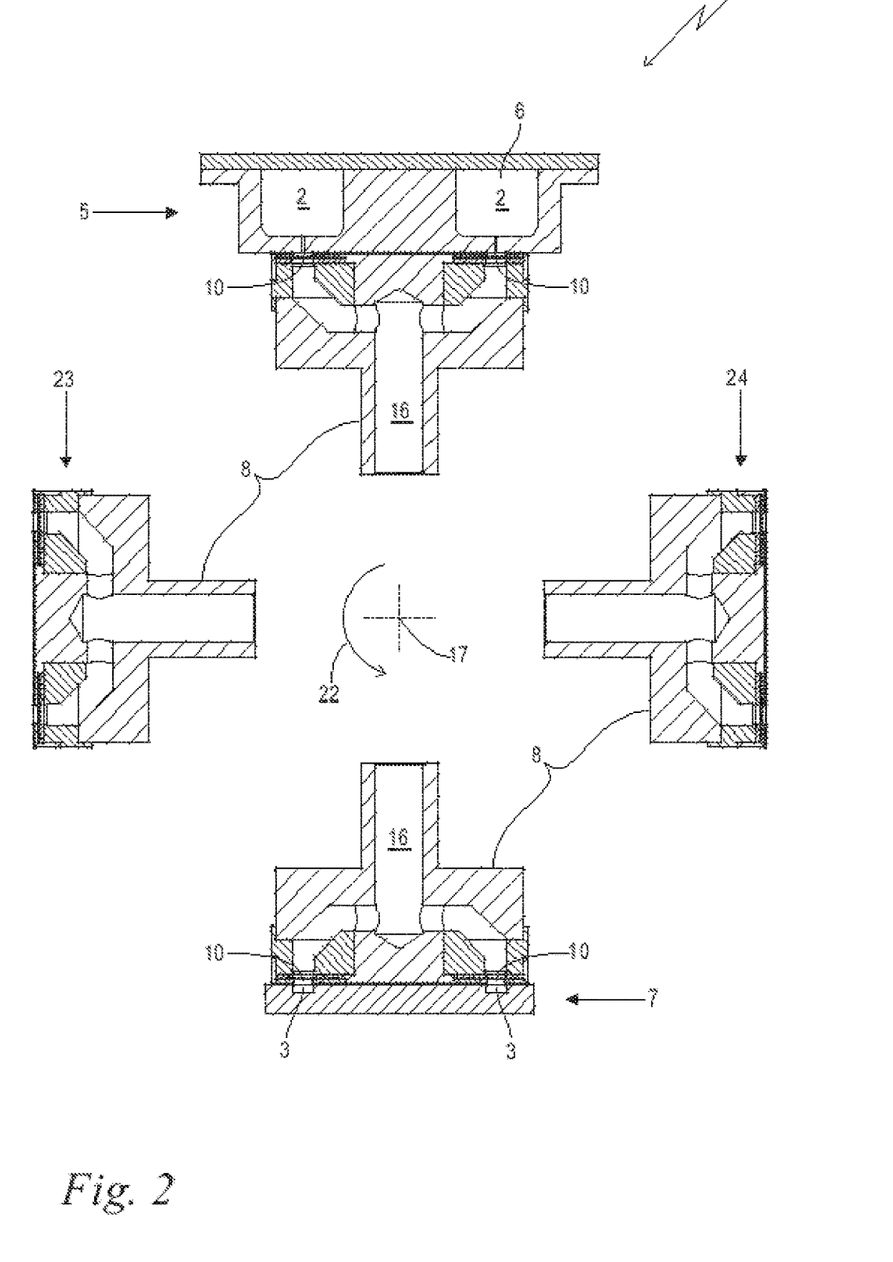
FIG. 2 shows, in a sectioned front view, the arrangement according to FIG. 1 with details for the design of the metering station and of the metering members which are combined to form a jointly movable unit.

FIG. 2 shows, in a sectioned front view, the arrangement according to FIG. 1 with details for the design of the metering station 5 and the metering members 8, which are combined to form a jointly moveable unit which is jointly pivotable here about the axis of rotation 17. The powder storage container 6 is also of annular design in accordance with the annular arrangement of the metering cavities 10, wherein, when the metering member 8 is placed below the metering station 5, the metering cavities 10 which are arranged in an annular manner come to lie below the powder storage container 6 which is likewise of annular design. In the event of a differing arrangement of the metering cavities 10, an analogous design of the powder storage container 6 is expedient.

As soon as the respective metering member 8 has reached the lower filling station 7 as a consequence of the pivoting movement about the axis of rotation 17 according to the arrow 22, the metering cavities 10 lie precisely above a respectively assigned target cavity 3.

Further details with regard to the overall view of the FIGS. 1 and 2 are also described further below.

Figure 3:
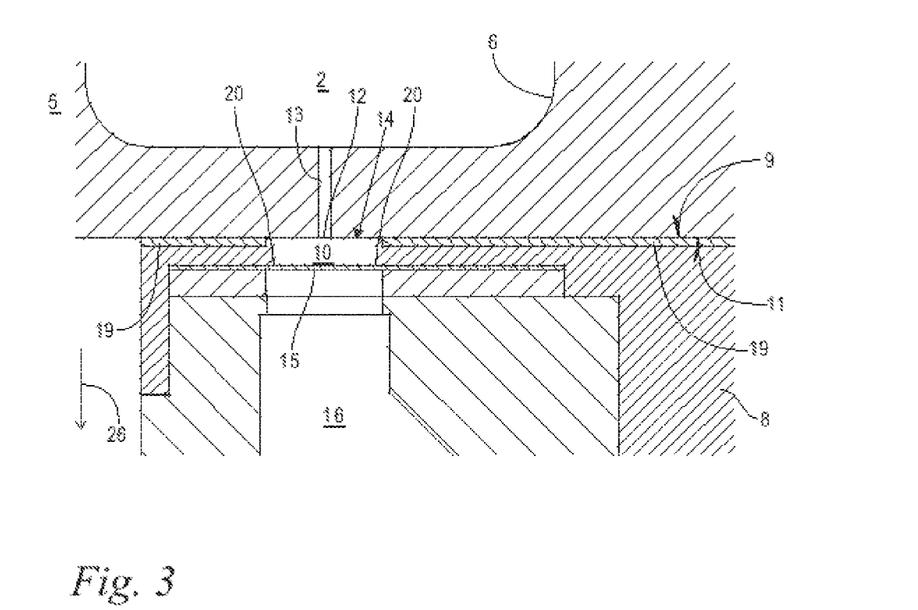
FIG. 3 shows, in an enlarged detailed view, the arrangement according to FIG. 2 in the region of the metering station with details for the interaction thereof with the metering member located therebelow.

FIG. 3 shows, in an enlarged detailed view, the arrangement according to FIG. 2 in the region of the metering station 5. It can be seen that the metering station 5 has, on the lower side thereof with respect to the weight direction, a flat contact surface 11 which is oriented horizontally and which is provided for sealing contact of the metering member 8 using the transfer surface 9 thereof. It becomes clear with simultaneous reference to FIGS. 1 and 2 that the transfer surface 9 of the respective metering member 8 lies perpendicularly to the radial direction emerging from the axis of rotation 17, and therefore the transfer surface 9 likewise lies horizontally in the upper 0° rotation position shown here. During the rotation operation of the metering members 8, there is a radial distance between the transfer surface 9 and the contact surface 11. As soon as the metering member 8 has reached the upper 0° rotation position according to FIG. 3, said metering member is moved from the bottom upward in the direction of the associated vertical axis 18 (FIG. 1) in accordance with the double arrow 25 toward the metering station 5, as a consequence of which the transfer surface 9 of the metering member 8 is pressed in a sealing manner against the contact surface 11 of the metering station 5. For an at least approximately air tight contact, the flat transfer surface 9 of the metering member 8 is closed at least in sections by an elastically flexible sealing material 19 which runs in a closed manner around the respective metering cavities 10, and is formed here, by way of example, in the form of a flat disc made of elastic silicone.

In a preferred embodiment, the sealing material 19 is solid and therefore air tight overall and can be pressed tightly with respect to the passage of air and powder against the flat contact surface 11 of the metering station 5 or against the seal surface 21 of the target cavities 3 in the filling station 7. A further preferred possibility resides in the use of a porous sealing material 19 which is air-permeable but is impermeable to the powder 2, in interaction (described in more detail further below) with the filling station 7. The two properties can also be combined with each other by, for example, a foamed sealing material 19 being used. At an appropriately high contact pressure, the pores of the elastic sealing material 19 are pressed together as a result of which the latter becomes impermeable to air and powder 2. At a lower contact pressure, the pores persist, as a result of which the same sealing material 19 is air-permeable, but is impermeable to the powder 2.

It may be expedient to form the transfer surface 9 completely from the sealing material 19. In the preferred exemplary embodiment shown, the metering cavities 10 each have an open side 14 on the side thereof which faces away from the axis of rotation 17 and here faces the metering station 5, said open side being surrounded by a collar-shaped edge 20 running around the open side 14 of the respective metering opening 12. The sealing material 19 runs around the collar-shaped edge 20 with respect to the circumferential direction of the open side 14, and therefore said sealing material does not come to lie between the edge 20 and the contact surface 11. As a consequence of the previously described contact pressure, the elastically flexible sealing material 19 is compressed until the edge 20, which is rigid by comparison and is metallic here, bears directly against the contact surface 11 of the metering station 5. In this case, the encircling edge 20 with high local surface pressure forms a boundary edge, which is present in an encircling and tight manner, for the respective metering cavity 10.

FIG. 3 furthermore shows that at least one powder channel 13 is formed in each case in the base of the powder storage container 6 in a manner corresponding to each metering cavity 10, said powder channel leading from the powder store of the powder storage container 6 to the lower contact surface 11 and opening there into a downwardly open metering opening 12. The metering openings 12 are also formed and distributed here in the contact surface 11 in a manner corresponding to the number and geometrical distribution of the metering cavities 10. However, this definition also includes the possibility that each metering cavity 10 can be assigned two or more metering openings 12 and powder channels 13.

It has already been mentioned previously that the metering openings 12 each have an open side 14 on the outside and at the top, in the 0° rotation position according to FIG. 3. In a manner opposite with respect thereto, i.e. at the bottom here and on the inside with respect to the radial direction lying perpendicularly to the axis of rotation 17 (FIG. 1), the metering cavities 10 are bounded by a base. The base of the target cavities 10 is formed at least in sections, here over the full area, by an air-permeable filter element 15. The filter element 15 is co-ordinated in respect of the permeability thereof to the powder 2 in such a manner that air, but not powder particles, can pass therethrough.

With reference again to FIG. 2, it can also be seen that a central pressure channel 16 is formed in each metering member 8, said pressure channel being connected to all of the metering cavities 10 via corresponding branches in a manner transmitting air pressure through the filter elements 15. A special characteristic of the pressure channel 16 consists in that the latter is arranged on the center axis of the respective metering member 8 while the metering cavities 10 are placed annularly around the center axis mentioned.

Accordingly, all of the branches of the pressure channel 16, the branches leading to the respective metering cavities 10, have at least approximately the same length, as a consequence of which the same pressure difference can be at least approximately applied to all of the metering cavities 10 using the central pressure channel 16.

The following method according to the application is explained on the basis of FIG. 3 with reference at the same time to the illustration according to FIGS. 1 and 2:

A metering member 8 is moved to the metering station and, as a consequence of the vertical movement in the direction of the vertical axis 18, is placed there with the flat transfer surface 9 thereof in a sealing manner against the flat contact surface 11 of the metering station 5. The open side 14 of the metering cavity 10 is covered here by the contact surface 11, and therefore a closed volume of the respective metering cavity 10 is formed or defined in conjunction with encircling circumferential walls and the filter element 15. Using the vertical movement mentioned, the sealing material is compressed between the basic body of the metering member 8 and the contact surface 11 of the metering station 5, as a result of which a connection which is tight against the passage of air and powder is provided between the metering member 8 and the metering station 5. In the case of the abovementioned sealing material 19 which is porous in an air-permeable manner, said sealing material can be compressed to such an extent that air and powder tightness occurs. Alternatively, however, a lower compression of the sealing material 19 which is porous in an air-permeable manner may suffice, with the air and powder tightness then being produced solely by the contact pressure of the edge 20 against the contact surface 11.

In this position, a negative pressure difference is then applied using the central pressure channel 16 to the powder 2 in the powder storage container 6 through the filter elements 15, the metering cavities 10 and the powder channels 13. The term selected here of "negative pressure difference" firstly generally means that a lower air pressure prevails in the pressure channel 16 than on the outside of the powder store. Conversely, a "positive pressure difference" means that a higher pressure prevails in the pressure channel 16 than in the powder storage container 6. A negative pressure difference can be brought about, for example, by the powder storage container 6 being closed and being charged on the inside with a positive pressure while a lower pressure relative thereto, for example atmospheric ambient pressure prevails in the pressure channel 16. Atmospheric ambient pressure preferably prevails in the powder storage container 6 while a negative pressure is formed in the pressure channel 16 using a negative pressure source, for example a vacuum pump or other device (not illustrated). In each case, the negative pressure difference results in the powder provided in the powder storage container 6 being sucked using the powder channels 13 into the metering cavities 10 and being retained there at the filter elements 15 while entrained air and the air previously located in the metering cavities escapes or is sucked up by the filter elements 15 and the pressure channel 16. By this action, all of the metering cavities 10 of an individual metering member 8 are completely filled at the same time with powder 2 and, in the process, are precisely metered volumetrically as a consequence of the defined volume of the individual metering cavities 10.

It may be expedient to maintain a continuous, consistent negative pressure difference during the filling of the metering cavities 10. At least one pulse-like negative pressure difference is preferably applied. It may also be expedient to combine one or more negative pressure pulses with a continuous negative basic pressure difference.

Following the filling of the metering cavities 10, the metering member 8 bearing against the metering station 5 is moved downward in the direction of the vertical axis 18 (FIG. 1) corresponding to an arrow 26 (FIG. 3) such that the transfer surface 9 is raised from the contact surface 11 of the metering station 5. Alternatively, it may also be expedient to initially leave the metering member in the position thereof and instead to raise the metering station. Both cases depend on a rising relative stroke taking place between metering member 8 and metering station 5. For the raising operation mentioned, it may be expedient temporarily to cancel the negative pressure difference so that the raising operation is not obstructed by the contact pressure forces resulting from the pressure difference. However, as soon as the metering member 8 with the transfer surface 9 thereof is raised from the contact surface 11 of the metering cavity 10, a negative pressure difference is re-applied. The metering member 8 is moved from the metering station 5 to the filling station 7 with said negative pressure difference being maintained, as can be seen in FIG. 2 and is illustrated in details in the enlarged detailed view according to FIG. 4. During the rotational movement lying in between, the maintaining of the negative pressure difference prevents the powder 2 located in the metering cavities 10 from dropping out of the open sides 14.

Figure 4:
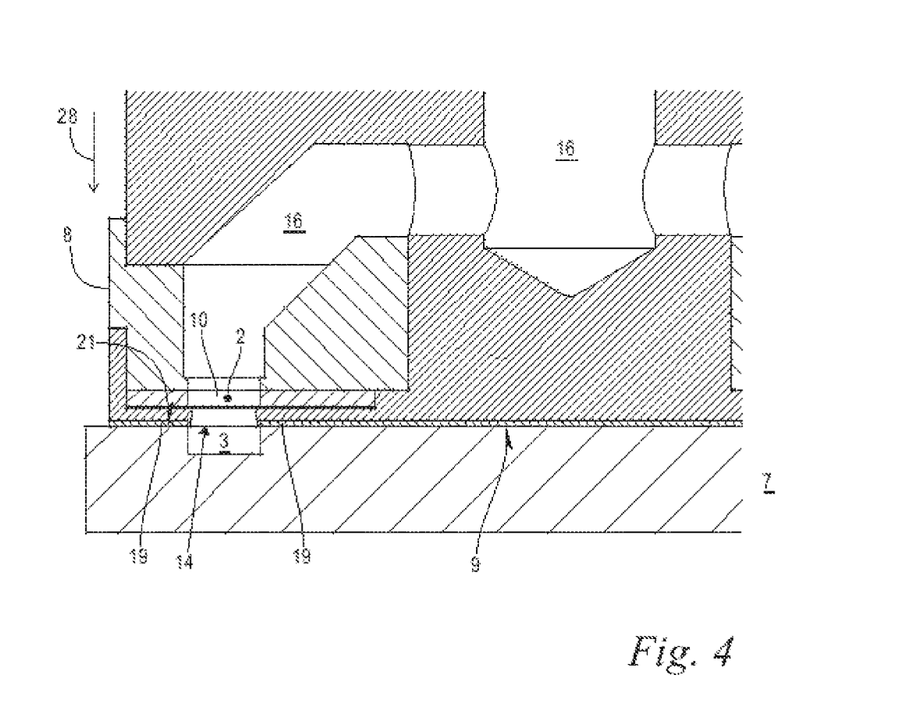
FIG. 4 shows, in an enlarged detailed view, the arrangement according to FIG. 2 in the region of the filling station with details for the interaction thereof with the metering member located thereabove.

When the filling station 7 or the 180° rotation position according to the illustration in FIG. 4 is reached, the transfer surface 9 of the metering member 8 and the open sides 14 of the metering cavities 10, which sides lie in the same plane, face downward in the weight direction, with the metering cavities 10 coming to lie exactly over one target cavity 13 each. Proceeding therefrom, the target cavities 3 are then filled, for which purpose the metered powder 2 is transferred from the metering cavities 10 into the respectively associated target cavities 3. In another embodiment, it may be expedient here to omit a vertical movement in the direction of the vertical axis 18 (FIG. 1), and therefore a distance remains between the transfer surface 9 and the upper edge of the target cavities 3. In a preferred embodiment, the metering member 8 is lowered in the direction of the vertical axis 18 (FIG. 1) according to an arrow 28 (FIG. 4) onto the target cavities 3, wherein the flat transfer surface 9 of the metering member 8 is pushed in a sealing manner against edges, in particular seal surfaces 21 of the target cavities. A relative stroke is especially also depended upon here, and this can also be brought about by raising the filling station 7. The transfer surface 9 and in particular the elastic sealing material 19 thereof cover the mentioned edges or the seal surface 21 of the target cavities 3 such that powder cannot pass onto them. An elastic sealing material 19 in air tight and powder tight form can also be used here. In the preferred case of the sealing material 19 which has already been described above and is porous in an air-permeable manner, if said sealing material is not compressed into an air tight state, the effect, however, can be achieved that the air displaced out of the target cavities 3 by the powder 2 filled into the latter can escape through the sealing material 19 while the sealing material 19, which is at the same time impermeable to the powder 2, prevents powder from escaping from the target cavities 3 and an undesirable action upon the seal surface 21 with powder 2.

In order to transfer the powder 2 from the metering cavities 10 into the target cavities 3, a corresponding pressure gradient can then be applied via the pressure channel 16. this may be a short pressure surge with a positive pressure difference or an air pressure oscillating between a positive and a negative pressure difference. Alternatively or in addition, it may be expedient to apply a mechanical pulse or a mechanical vibration to the powder 2 located in the metering cavities 10. In all cases, the powder is loosened in the metering cavities 10 such that the powder drops from there into the target cavities 3 under the action of the weight. After an optional raising movement counter to the arrow 28 (FIG. 4), the metering member 8 is then moved back to the metering station 5 using a pivoting or rotational movement about the axis of rotation 17 corresponding to the arrow 22 (FIG. 1) where the above-described metering and filling cycle begins again.

The optional intermediate stations 23, 24 corresponding to the illustration according to FIGS. 1 and 2 have already been mentioned previously. The first intermediate station 23 which lies in the direction of rotation corresponding to the arrow 22 between the metering station 5 and the filling station 7 can be designed as a checking station in which it is checked whether all of the metering cavities 10 have actually been correctly filled with powder 2. The second intermediate station 24 which lies with respect to the direction of rotation according to the arrow 22 between the lower filling station 7 and the upper metering station 5 can be designed, for example, as an inspection station in which it is checked whether all of the metering cavities 10 have previously transferred their amount of powder in the filling station 7 to the target cavities 3, or whether residual quantities of powder 2 still remain in the metering cavities 10. Of course, further stations, for example in the form of cleaning stations or the like, are also useable within the context of the application.

Figure 5:
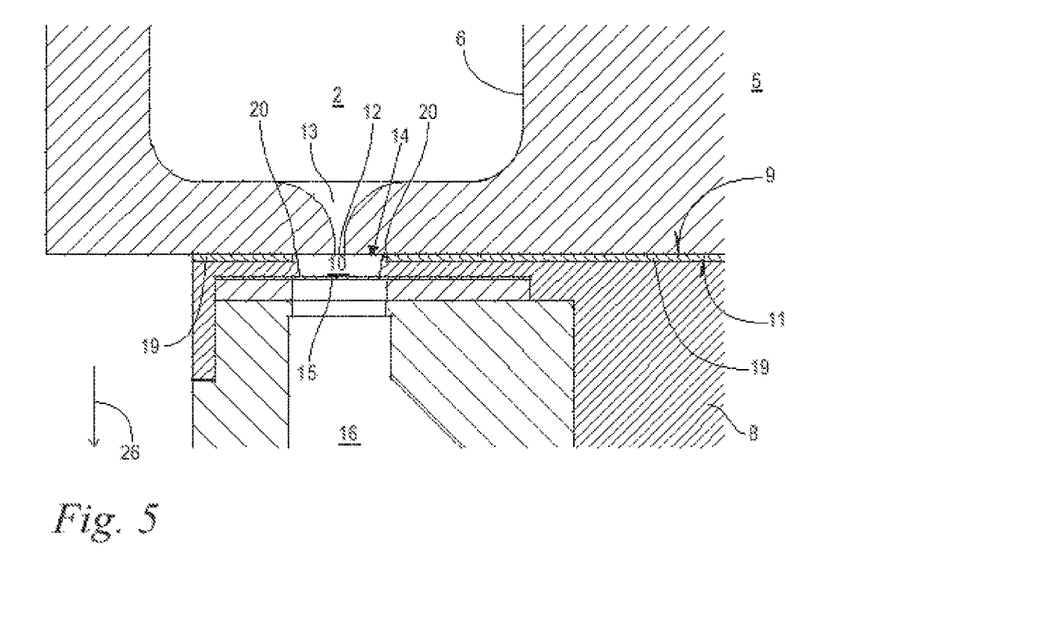
FIG. 5 shows a variant of the arrangement according to FIG. 3 with a powder channel of rounded configuration.
Figure 6:
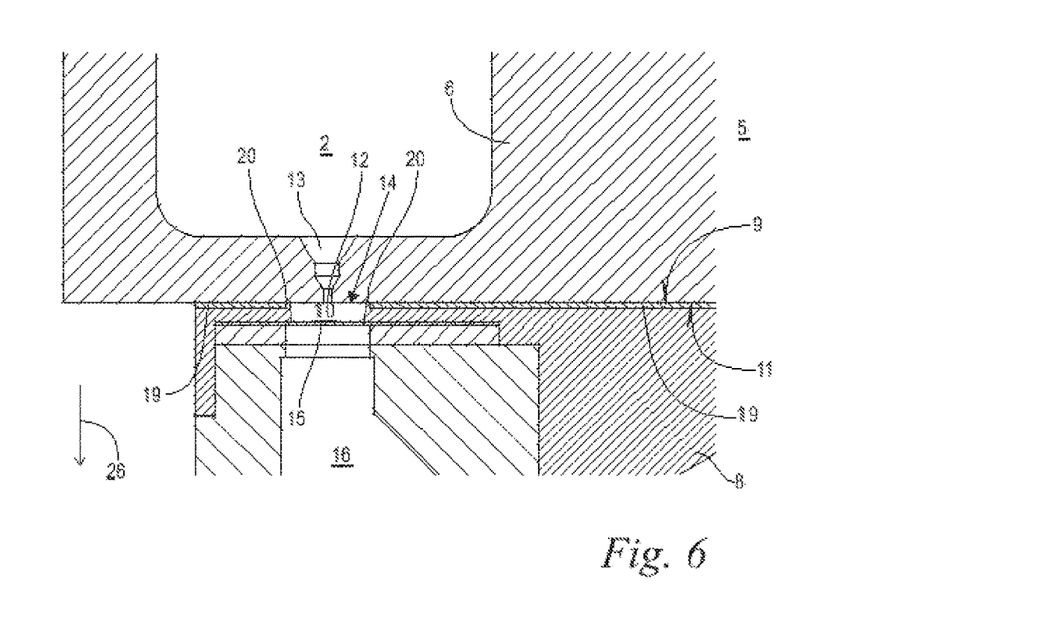
FIG. 6 shows a further variant of the arrangement according to FIGS. 3 and 5 with a powder channel of stepped configuration.

FIGS. 5 and 6 also show variants of the arrangement according to FIG. 3. wherein, in FIG. 3, the powder channel is formed cylindrically with a cross section which is constant along the running length. In a departure therefrom, the powder channel 13 in the exemplary embodiment according to FIG. 5 has an expanded inlet region which is rounded in longitudinal section and from which the cross section of the powder channel 13 tapers as far as the metering opening 12. Alternatively, in FIG. 6, a stepped cross-sectional tapering of the powder channel 13 toward the metering opening 12 is provided with conical and cylindrical sections. By this form or by comparable longitudinal and cross-sectional forms, the flowability of the powder 2 through the powder channel 13 when a negative pressure difference is present can be improved while, at the same time, if the negative pressure difference is missing, an unintentional trickling out of the powder can be reliably avoided. The exemplary embodiments according to FIGS. 5 and 6 correspond in the remaining features and reference numbers to that according to FIGS. 1 to 4.

The foregoing description of preferred embodiments has been presented for purposes of illustration and description only. It is not intended to be exhaustive or to limit the invention to the precise form disclosed, and modifications and variations are possible and/or would be apparent in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto and that the claims encompass all embodiments of the invention, including the disclosed embodiments and their equivalents.

The invention claimed is:

1. A metering device for the volumetric metering of a pharmaceutical powder and filling of a plurality of target cavities with the metered powder, wherein the plurality of target cavities are arranged in a common plane, comprising:
a metering station, wherein the metering station comprises a powder storage container,
a filling station, wherein the filling station comprises the plurality of target cavities, and
a movable metering member, wherein the metering member configured for cyclical movement between a first spatial arrangement and a second spatial arrangement, wherein in the first spatial arrangement the movable metering member engages the metering station and wherein in the second spatial arrangement the movable metering member engages the filling station, wherein the metering member comprises a flat transfer surface, wherein a plurality of metering cavities are arranged in the flat transfer surface, wherein the number and geometric distribution of the metering cavities corresponds to the number and the geometric distribution of the target cavities,
wherein the metering station further comprises a flat contact surface that provides a sealing contact of the metering member through engagement with the flat transfer surface, wherein metering openings are formed in the contact surface, wherein the number and geometric distribution of the metering openings corresponds to the number and geometric distribution of the metering cavities, wherein powder channels connect the powder storage container and the metering openings,
wherein, in the plane of the transfer surface, the metering cavities each have an open side and a base opposite from the open side, wherein the base of the respective metering cavity is formed at least in sections by an air-permeable filter element, wherein a central pressure channel is formed in the metering member and is connected in a pressure-transmitting manner to the metering cavities through the filter elements.

2. The metering device according to claim 1, wherein the metering member is displaceable in the direction of a vertical axis such that the metering member may move toward the flat contact surface of the metering station and away from the flat contact surface.

3. The metering device according to claim 1, wherein the flat transfer surface of the metering member is formed at least in part by an elastically flexible sealing material encircling the metering cavities in a closed manner.

4. The metering device according to claim 3, wherein the sealing material is airtight.

5. The metering device according to claim 3, wherein the sealing material is porous in an air-permeable manner.

6. The metering device according to claim 3, wherein the metering cavities comprise an inflexible, encircling edge, wherein the edge is provided for direct contact against the contact surface of the metering station, and wherein the sealing material encircles the edge.

7. A metering system comprising the metering device according to claim 1 and an associated member of target cavities arranged in a common plane.

8. A method for metering a pharmaceutical powder and for filling a plurality of target cavities arranged in a common plane using the metering device according to claim 1, said method comprising:

placing the metering member with the flat transfer surface a in sealing manner onto the flat contact surface of the metering station;

applying a negative pressure difference to the powder in the powder storage container through the filter elements, the metering cavities, and the powder channels by using the central pressure channel, wherein the metering cavities are simultaneously filled with the powder from the powder storage container through the powder channels, wherein the powder is retained at the filter elements;

moving the metering member from the metering station to the filling station while maintain a negative pressure difference, and bringing the metering cavities t into overlap with associated target cavities;

eliminating the negative pressure difference such that the powder is brought from the metering cavities into the respectively assigned target cavities; and, moving the metering member back to the metering station.

9. The method according to claim 8, further comprising:
moving the metering member linearly in the direction of the vertical axis toward the flat contact surface of the metering station;
filling the metering cavities with the powder by charging with the negative pressure difference;
removing the metering member linearly in the direction of the vertical axis from the flat contact surface of the metering station, wherein the negative pressure difference is eliminated; and,
moving the metering member from the metering station to the filling station with a negative pressure difference being reapplied and maintained.

10. The method according to claim 8, wherein a pulse-like negative pressure difference is applied at the metering station for filling the metering cavities with the powder.

11. The method according to claim 8, wherein a pressure surge with a positive pressure difference, an air pressure oscillating between a positive and a negative pressure difference, a mechanical pulse or a mechanical vibration is applied to the powder located in the metering cavities at the filling station for transferring the powder from the metering cavities into the target cavities.

12. The method according to claim 8, wherein the metering member is pressed with the flat transfer surface thereof in a sealing manner against seal surfaces of the target cavities at the filling station.

13. A metering device for the volumetric metering of a pharmaceutical powder and filling of a plurality of target cavities with the metered powder, wherein the plurality of target cavities are arranged in a common plane, comprising:
a metering station, wherein the metering station comprises a powder storage container,
a filling station, wherein the filling station comprises the plurality of target cavities, and
a movable metering member, wherein the metering member is cyclically movable from the metering station to the filling station and back again, wherein the metering member comprises a flat transfer surface, wherein a plurality of metering cavities are arranged in the flat transfer surface, wherein the number and geometric distribution of the metering cavities corresponds to the number and the geometric distribution of the target cavities,
wherein the metering station further comprises a flat contact surface that provides a sealing contact of the metering member through engagement with the flat transfer surface, wherein metering openings are formed in the contact surface, wherein the number and geometric distribution of the metering openings corresponds to the number and geometric distribution of the metering cavities, wherein powder channels connect the powder storage container and the metering openings,
wherein, in the plane of the transfer surface, the metering cavities each have an open side and a base opposite from the open side, wherein the base of the respective metering cavity is formed at least in sections by an air-permeable filter element, wherein a central pressure channel is formed in the metering member and is connected in a pressure-transmitting manner to the metering cavities through the filter elements,
wherein the metering member is pivotable about an axis of rotation, wherein, in a 0° rotational position, the metering member lies with the flat transfer surface facing upward below the metering station, and wherein, in a 180° rotational position, the metering member lies with the flat transfer surface facing downward above the metering station.

14. The metering device according to claim 13, wherein a plurality of metering members are arranged around the axis of rotation and together form a jointly rotatable unit that allows for a sequential approach of the metering station and the filling station.

15. The metering device according to claim 13, wherein the metering member is displaceable in the direction of a vertical axis such that the metering member may move toward the flat contact surface of the metering station and away from the flat contact surface.

16. The metering device according to claim 13, wherein the flat transfer surface of the metering member is formed at least in part by an elastically flexible sealing material encircling the metering cavities in a closed manner.

17. The metering device according to claim 16, wherein the sealing material is airtight.

18. The metering device according to claim 16, wherein the sealing material is porous in an air-permeable manner.

19. The metering device according to claim 16, wherein the metering cavities comprise an inflexible, encircling edge, wherein the edge is provided for direct contact against the contact surface of the metering station, and wherein the sealing material encircles the edge.

20. A metering system comprising the metering device according to claim 13 and an associated member of target cavities arranged in a common plane.

* * * * *